(12) United States Patent
Sharma et al.

(10) Patent No.: US 11,170,891 B2
(45) Date of Patent: Nov. 9, 2021

(54) IMAGE GENERATION FROM A MEDICAL TEXT REPORT

(71) Applicant: Siemens Healthcare GmbH, Erlangen (DE)

(72) Inventors: Puneet Sharma, Princeton Junction, NJ (US); Dominik Neumann, Erlangen (DE); Ruth J. Soenius, New York, NY (US); Ulrich Hartung, Langensendelbach (DE)

(73) Assignee: Siemens Healthcare GmbH, Erlangen (DE)

( * ) Notice: Subject to any disclaimer, the term of this patent is extended or adjusted under 35 U.S.C. 154(b) by 177 days.

(21) Appl. No.: 16/253,662

(22) Filed: Jan. 22, 2019

(65) Prior Publication Data
US 2019/0237184 A1    Aug. 1, 2019

(30) Foreign Application Priority Data

Jan. 29, 2018   (EP) .................................... 18153991

(51) Int. Cl.
| | |
|---|---|
| G16H 30/40 | (2018.01) |
| G16H 10/60 | (2018.01) |
| G06F 40/289 | (2020.01) |
| G16H 15/00 | (2018.01) |

(52) U.S. Cl.
CPC ........... *G16H 30/40* (2018.01); *G06F 40/289* (2020.01); *G16H 10/60* (2018.01); *G16H 15/00* (2018.01)

(58) Field of Classification Search
CPC .................................................... G16H 15/00
See application file for complete search history.

(56) References Cited

U.S. PATENT DOCUMENTS

| | | | | |
|---|---|---|---|---|
| 9,754,220 | B1* | 9/2017 | Brestoff | G06F 40/40 |
| 10,503,867 | B1* | 12/2019 | Walker | G06F 40/284 |
| 2006/0277073 | A1* | 12/2006 | Heilbrunn | G16H 15/00 705/3 |
| 2007/0237377 | A1 | 10/2007 | Oosawa | |
| 2009/0248441 | A1* | 10/2009 | Okada | G06F 19/321 705/2 |
| 2010/0114597 | A1* | 5/2010 | Shreiber | G06F 19/321 705/2 |
| 2011/0199390 | A1* | 8/2011 | Iizuka | G16H 50/20 345/629 |
| 2012/0035963 | A1 | 2/2012 | Qian et al. | |

(Continued)

OTHER PUBLICATIONS

European Search Report dated Jul. 10, 2018 in corresponding European Patent Application No. 18153991.7.

(Continued)

*Primary Examiner* — Wen W Huang (57) ABSTRACT

A method of generating a first image from a medical text report comprises acquiring a medical text report comprising one or more natural language statements; analysing the medical text report, using a computer-implemented analysis process, to determine for each natural language statement whether the statement satisfies a predetermined criterion with respect to a first medical finding; and responsive to a determination that a said statement satisfies the predetermined criterion, adding an image representing the first medical finding to an image template, to generate the first image. Also disclosed is an apparatus and computer program.

19 Claims, 6 Drawing Sheets

(56) References Cited

U.S. PATENT DOCUMENTS

| | | | | |
|---|---|---|---|---|
| 2017/0293734 | A1* | 10/2017 | Potter | G06F 40/30 |
| 2018/0196873 | A1* | 7/2018 | Yerebakan | G16H 10/60 |
| 2019/0034589 | A1* | 1/2019 | Chen | G16H 10/60 |
| 2019/0130073 | A1* | 5/2019 | Sun | G16H 50/70 |
| 2019/0179883 | A1* | 6/2019 | Bao | G16H 50/20 |
| 2019/0310981 | A1* | 10/2019 | Sevenster | G06F 16/2465 |
| 2020/0303072 | A1* | 9/2020 | Drokin | G16H 50/20 |

OTHER PUBLICATIONS

"Eagle Eye" BiTeM. http://bitem.hesge.ch/resource/eagli-eagle-eye. Accessed Mar. 7, 2018.
"Facebook Research DrQA" GitHub. https://github.com/facebookresearch/DrQA. Accessed Mar. 7, 2018.
"Natural Language Question Answering System" The START, http://start.csail.mit.edu/index.php. Accessed Mar. 7, 2018.
"Question Answering" Wikipedia. https://en.wikipedia.org/wiki/Question_answering. Accessed Mar. 7, 2018.
"The DeepQA Project" Research IBM. https://www.research.ibm.com/deepqa/deepqa.shtml. Accessed Mar. 7, 2018.
Reed, Scott, et al. "Generative adversarial text to image synthesis." arXiv preprint arXiv: 1605.05396 (2016) p. 1-8.
U.S. Appl. No. 15/957,143, filed Apr. 19, 2018.

* cited by examiner

FIG 1

| 252 Statement | Stenosis 260 | | |
| --- | --- | --- | --- |
| | 254 Presence | 256 Severity | 258 Location |
| Atherosclerotic calcification at the origin of the left main coronary artery without evidence of stenosis. | N | | |
| Diffuse scattered calcification of the left anterior descending coronary artery with severe stenosis at the mid LAD. Contrast is seen distal to the area of stenosis. | Y | severe | mid |
| Scattered atherosclerotic calcifications without stenosis. | N | | |
| Atherosclerotic calcification of the distal right coronary artery with at least moderate stenosis. This is a right dominant system | Y | moderate | |
| No evidence of stenosis | N | | |
| No evidence of stenosis | N | | |
| No evidence of stenosis | N | | |

FIG 6

IMAGE GENERATION FROM A MEDICAL TEXT REPORT

This application claims the benefit of European Patent Application No. 18153991.7, filed Jan. 29, 2018, which is hereby incorporated by reference in its entirety.

TECHNICAL FIELD

The present invention relates to generating images, and more specifically to generating an image from a medical text report, such as a radiology report.

BACKGROUND

Medical text reports, for example radiology reports, are used in the medical field to communicate information between medical professionals. For example, a patient's physician may refer a patient for certain medical imaging, for example Computed Tomography Angiography (CTA). A radiographer then carries out the medical imaging of the patient and a radiologist then reads or interprets the resulting image to produce a text-based radiology report of their findings. A medical finding may be defined as an observation made of the patient, for example by a doctor, for example as a result of examination, imaging, or other tests of the patient. The radiology report is then provided to the referring physician. The referring physician may then make a diagnosis of a condition of the patient based on the radiology report. 99

The radiology report is often the main form of communication between the radiologist and a referring physician. The reports include narrative text dictated by the radiologist, and, in some cases, are structured according to a predefined format. While preparing the report, the radiologist balances two opposing aspects: to be as comprehensive as possible, and still ensure that all the key findings are communicated succinctly to the referring physician. This can result in reports that are too verbose, with some key findings (positive or negative) often hidden or difficult to appreciate among the narrative text. This can have severe consequences such as misdiagnosis or missed findings.

Increasingly, medical text reports, such as radiology reports, have another audience in addition to the referring physician, namely the patient. For efficient communication with the patient, it is important that the reports are easily understandable to a non-medical professional (e.g. the patient). However, radiology reports often cannot fulfil these competing demands and constraints. An existing attempt to address this is for the radiologist to adopt guidelines, which can result in structured reports having a predefined format. However, the structured reports still suffer from the drawbacks that it is difficult to extract the most relevant information both for medical professionals and non-medical professionals, and potentially highly important secondary findings may still be difficult to appreciate amongst the narrative text, possibly resulting in misdiagnosis.

Presenting medical reports using images, illustrating relevant medical information, for example, would mitigate the above issues. It is therefore desirable to provide an efficient method of generating such images.

SUMMARY

According to a first aspect of the present invention, there is provided a method of generating a first image from a medical text report, the method comprising: acquiring a medical text report comprising one or more natural language statements; analysing the medical text report, using a computer-implemented analysis process, to determine for each natural language statement whether the statement satisfies a predetermined criterion with respect to a first medical finding; and responsive to a determination that a said statement satisfies the predetermined criterion, adding an image representing the first medical finding to an image template, thereby to generate the first image.

Optionally, the analysis process comprises a text classification based algorithm, and wherein the first predetermined criterion comprises that the statement is classified by the text classification algorithm as positive with respect to the first medical finding.

Optionally, the method comprises: analysing the medical text report, using the computer-implemented analysis process, to determine, for each natural language statement determined as satisfying the predetermined criterion with respect to a first medical finding, one or more first parameters associated with the first medical finding; and wherein the adding the image representing the first medical finding to the image template is based at least in part on the determined one or more first parameters.

Optionally, at least one of the first parameters comprises a location parameter relating to a location of the first medical finding; and the method comprises: determining, based on the location parameter, a section of the image template to which the image representing the first medical finding is to be added; and adding the image representing the first medical finding to the determined section of the image template.

Optionally, the first parameters comprise one or both of a type parameter relating to a type of the first medical finding and an extent parameter relating to an extent of the first medical finding; and the adding the image representing the first medical finding to the image template is based at least in part on one or both of the type parameter and the extent parameter.

Optionally, the adding the image representing the first medical finding to the image template comprises overlaying the image template with the image representing the first medical finding.

Optionally, the medical text report is a radiology report.

Optionally, the image template comprises a pictogram representing a patient anatomy to which the radiology report is directed; and wherein the image representing the first medical finding is added to the pictogram so as to indicate the first medical finding on the pictogram.

Optionally, the computer-implemented analysis process comprises a machine learning based algorithm.

Optionally, the method comprises training the machine learning based algorithm based on a database of textual statements, each statement being annotated with a ground-truth label corresponding to the first medical finding.

Optionally, the training comprises: generating, based on a plurality of medical text reports, one or more word-embeddings for one or more words of the plurality of medical text reports; and determining, for each of the textual statements, one or more said word embeddings representative of the textual statement; and wherein the training is based on the word-embeddings representative of each textual statement.

Optionally, the training is implemented using a Long-Short-Term-Memory based Recurrent Neural Network architecture.

Optionally, the method comprises: generating a medical report, the medical report comprising the first image.

According to a second aspect of the present invention, there is provided an apparatus for generating a first image from a medical text report; the apparatus being configured to perform the method according to the first aspect.

According to a third aspect of the present invention, there is provided a computer program comprising instructions which when executed on a computer cause the computer to perform the method according to the first aspect.

Further features and advantages of the invention will become apparent from the following description of preferred embodiments of the invention, given by way of example only, which is made with reference to the accompanying drawings.

DETAILED DESCRIPTION

Figure 1:
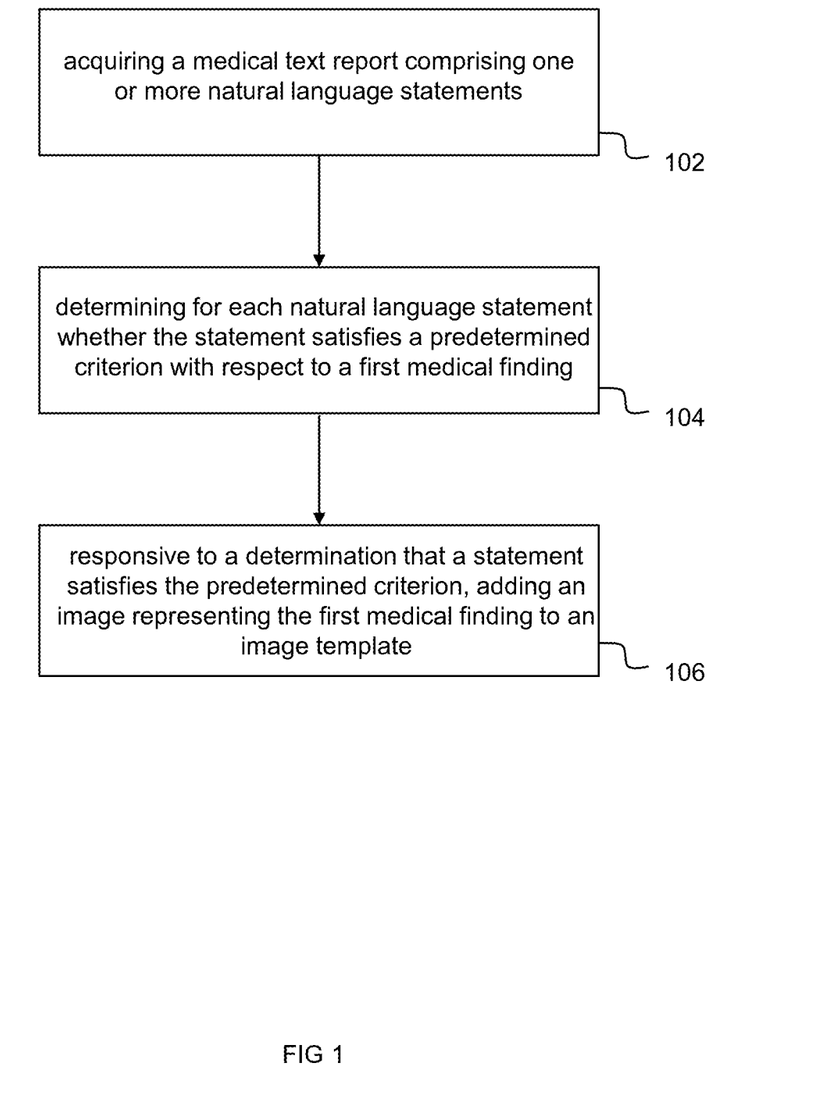
FIG. 1 illustrates schematically a flow diagram of a method according to an example of the present invention.

FIG. 1 illustrates schematically a flow diagram of steps of a method of generating a first image from a medical text report, according to an example.

Figure 3:
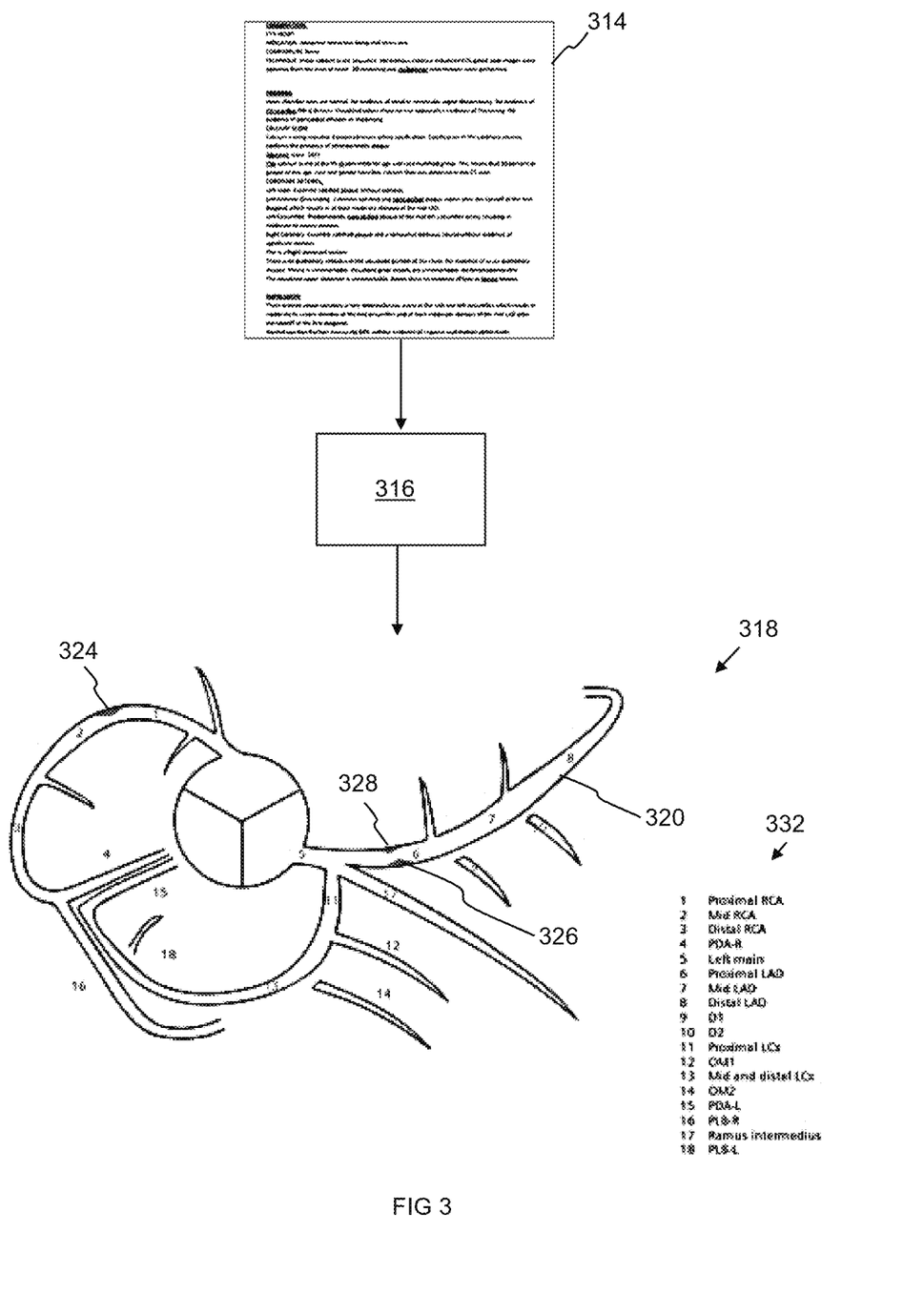
FIG. 3 illustrates schematically a process for generating an image from a medical text report, according to first example.

The method comprises, in step 102, acquiring a medical text report comprising one or more natural language statements (a medical text report is not shown in FIG. 1, but see e.g. the medical text report 314 of FIG. 3).

The medical text report may be a radiology report. For example, a radiographer may carry out medical imaging of a patient and a radiologist may read or interpret the resulting image or images and produce a text report of their findings.

The medical imaging may comprise, for example, Computed Tomography (CT) scanning, for example Computed Tomography Angiography (CTA), or may comprise, for example, Magnetic Resonance Imaging (MRI), for example stress perfusion cardiac MRI.

The radiology report may include narrative text dictated by the radiologist. The radiology report may be structured according to a predefined format, for example may include narrative text under one or more different sections of the report, for example an "Examination" section detailing the type of medical imaging used, a "Findings" section detailing the medical findings of the radiologist, and an "Impression" section detailing the initial opinion of the radiologist on the condition of the patient. A medical finding may be defined as an observation made of the patient by a doctor (e.g. the radiologist), for example as a result of examination, imaging, or other test of the patient (e.g. radiography). For example, a medical finding of a radiologist may be a clinically significant observation made about the patient, for example a particular disease state or other medical feature of the patient, based on medical imaging of the patient or other examinations. For example, a medical finding may comprise, the presence or absence, type, location and/or a severity of the disease state, clinical abnormalities or other medical feature of the patient as surveyed by the radiologist.

The medical findings may be included in one or more natural language statements of the report. A natural language statement may be, for example, a sentence in a natural language, for example English. For example, a natural language statement of a stress perfusion cardiac MRI radiology report may be "Stress perfusion imaging shows perfusion defect in the basal to apical septum and apical anterior wall." A medical finding of this natural language statement may be that the presence of a perfusion defect, and/or that there is a perfusion defect in the basal to apical septum wall, and/or that that there is a perfusion defect in the apical anterior wall. As another example, a natural language statement of a Computed Tomography Angiography (CTA) radiology report may be "Diffuse scattered calcification of the left anterior descending (LAD) coronary artery with severe stenosis at the mid LAD". A medical finding of this natural language statement may be that there is a stenosis, and/or that there is a severe stenosis, and/or that there is a severe stenosis at the mid left anterior descending coronary artery.

The method comprises, in step 104, analysing the medical text report, using a computer-implemented analysis process, to determine for each natural language statement whether the statement satisfies a predetermined criterion with respect to a first medical finding.

The computer implemented analysis process may comprise natural language processing. For example, the computer-implemented analysis process may comprise a text classification based algorithm, and the first predetermined criterion may comprise that the statement is classified by the text classification algorithm as positive with respect to the first medical finding. For example, a statement may be classified as positive with respect to the first medical finding if the algorithm determines that the statement positively indicates the presence of the first medical finding. For example, the first medical finding may be "stenosis". The first predetermined criterion may be that the statement is classified as positive with respect to "stenosis", for example that the statement positively indicates the presence of stenosis. For example, the statement "Diffuse scattered calcification of the left anterior descending (LAD) coronary artery with severe stenosis at the mid LAD" may be classified as positive with respect to the finding "stenosis" and hence may be determined as satisfying the predetermined criterion, whereas the statement "No evidence of stenosis" may not be classified as positive with respect to the finding "stenosis" (e.g. may be classified instead as negative with respect to the finding "stenosis"), and hence may not be determined as satisfying the predetermined criterion. It is noted that both of the above example statements include the word "stenosis", but only the first example statement is classified as positive with respect to the finding "stenosis".

The computer-implemented analysis process may comprise a machine learning based algorithm. For example, the machine learning algorithm may comprise supervised learning, which may comprise inferring a function from labelled training data comprising training examples. For example, the method may comprise training the machine learning based algorithm based on a database of textual statements, each statement being annotated with a ground-truth label corresponding to the first medical finding. As one example, the training may be implemented using a Recurrent Neural Network architecture, in which an internal memory may be used to process arbitrary sequences of inputs. For example, the training may be implemented using a Long Short-Term Memory (LSTM) based Recurrent Neural Network architecture, for example comprising one or more LSTM cells for remembering values over arbitrary time intervals.

Figure 2:
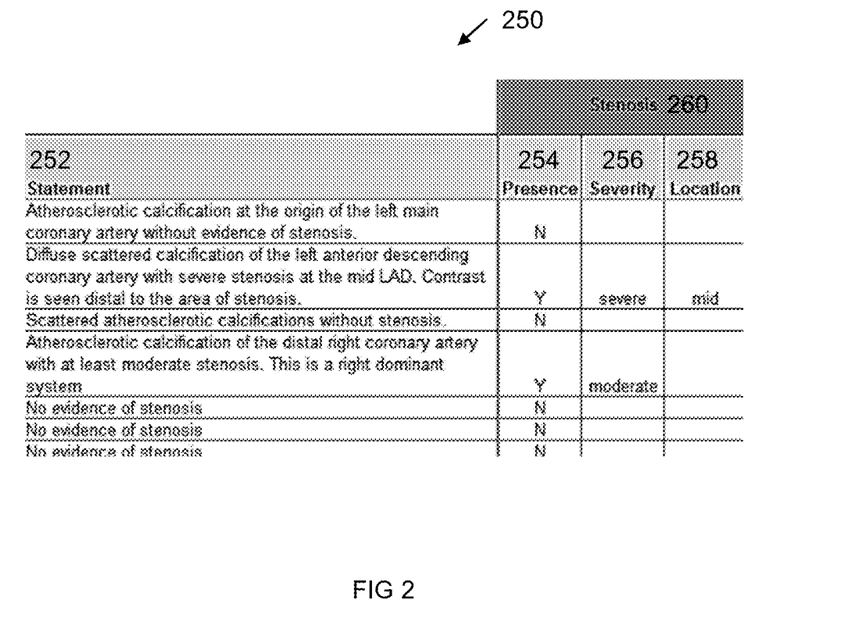
FIG. 2 illustrates schematically a table representing a database of textual statements according to an example.

FIG. 2 illustrates schematically a table 250 representing training data according to an example. The training data may be stored in a database (not shown). A first column 252 of the table 250 lists natural language statements. The statements may be from a plurality of radiology reports pre-collected as a training data set and corpus for the machine learning algorithm. The second column 254, third column 256, and fourth column 258 of the table 250 list ground-truth labels corresponding to a first medical finding 250 for those statements. In this example, the first medical finding 250 is "stenosis", the second column 254 lists ground-truth labels for the (positive) presence of "stenosis" indicated in the corresponding natural language statement of the first column 252, the third column 256 lists ground-truth labels for the severity of stenosis indicated in the corresponding natural language statement of the first column 252, and the fourth column 258 lists ground-truth labels for the location of stenosis indicated in the corresponding natural language statement of the first column 252. For example, for the statement in the first column 252 of "Diffuse scattered calcification of the left anterior descending (LAD) coronary artery with severe stenosis at the mid LAD", the second column 254 reads "Y" indicating a (positive) presence of "stenosis" for the statement, the third column reads "severe" indicating the severity of the stenosis for the statement, and the fourth column reads "mid" indicating the location of the stenosis for the statement. However, for the statement of the first column 252 of "No evidence of stenosis", the second column 254 reads "N" indicating a negative presence of "stenosis" for the statement, and the third column 256 and the fourth column 258 are blank.

Each statement of the training data may represent an input object, and the corresponding ground-truth label a supervisory signal, for the machine learning algorithm. The machine learning algorithm may analyse the training data to produce an inferred function, which may then be used for classifying the natural language statements of a medical text report to be analysed.

For example, the computer-implemented analysis process may comprise a linguistic model, where different linguistic models may be generated using different corpora of training data. In one example, training the machine learning algorithm comprises acquiring a plurality of medical text reports as training data (for example pre-existing relevant radiology reports), and segmenting one or more words from the plurality of medical text reports to generate a vocabulary of words. One or more word-embeddings may then be generated for one or more words of the generated vocabulary of words. The word-embeddings may map words or phrases from the vocabulary to vectors of real numbers. The training may then comprise determining, for each of the statements of the training data, one or more word-embeddings representative of the textual statement, and the training may be based on the word-embeddings representative of each textual statement. For example, the determined one or more word-embeddings (i.e. vectors of real numbers) representative of a textual statement may be used as an input object, and the corresponding ground-truth label used as a supervisory signal, for training the machine learning algorithm to produce an inferred function for mapping word embeddings onto one or more text classifications.

The computer-implemented analysis process may comprise applying the inferred function (either provided by the trained machine learning algorithm or otherwise) to word-embeddings for words or phrases of the natural language statements of the medical text report to be analysed, and determining whether the statement satisfies the predetermined criterion with respect to a first medical finding, for example whether the statement is classified as positive with respect to the first medical finding.

Returning again to FIG. 1, the method comprises, at step 106, responsive to a determination that the natural language statement satisfies the predetermined criterion, adding an image representing the first medical finding to an image template, thereby to generate the first image.

As described in more detail below, the image template may comprise, for example, a pictogram representing a patient anatomy to which the radiology report is directed, or a plot such as polar plot template comprising regions or axes relating to the patient anatomy to which the radiology report is directed. The image representing the first medical finding may be added to the image template so as to indicate the first medical finding on the pictogram. For example, an image representing a stenosis (i.e. a narrowing in a blood vessel or other structure) may be added to a coronary pictogram template, so as to indicate the medical finding of "stenosis" from a statement of the radiology report on the pictogram.

The generated first image, comprising the image template and the image representing the first medical finding added thereto, may then be output into a further or "enhanced" report, for example comprising the text of the radiology report as well as the generated first image (described in more detail below with reference to FIG. 6).

The generated first image may help understanding of the overall context, disease state, and severity of the findings of the radiology report, for both medical professionals and non-medical professionals, and hence reduce the risk of misunderstanding, misdiagnosis or missed findings.

The radiology report may be generated by the radiologist by analysing or reading a medical scan image, for example a CT scan image or the like. The medical scan image may be difficult to interpret for the referring physician or non-medical professional, for example as it may include irrelevant visual information, and/or the relevant visual information may be subtle. However, generating the first image by adding an image representing the first medical finding of the radiology report to an image template may allow an image to be produced that is clearer with respect to the important visual information contained in the medical scan image as compared to the medical scan image itself. An improved image may therefore be produced.

Further, the first image being based on an image template to which the image representing the first medical finding is added, allows for the graphic representation of the findings of the medical text report to be generated efficiently. For example, the image template may be stored and accessed recurrently for the generation of first images for multiple text reports, and the image generation process may comprise adding the image representation to the image template, which may be computationally efficient. For example, this may be more computationally efficient than, for example synthesizing a graphical representation of the natural language statements ab initio.

The adding the image representing the first medical finding to the image template may comprise overlaying the image template with the image representing the first medical finding. This overlaying may be a computationally efficient process for generating the first image. For example, this may be more computationally efficient as compared to synthesis of an image ab initio, or modification, for example recursive modification, of an image.

FIG. 3 illustrates schematically process including a generated first image 318 according to an example.

The process of FIG. 3 begins with the medical text report 314, which in this example is a Computed Tomography Angiography (CTA) radiology report 314, comprising natural language statements. The medical text report 314 is input into a computer-implemented analysis process block 316. The analysis process block 316 may perform the method described above with reference to FIGS. 1 and 2. For example, the process block 316 may analyse the radiology report 314 to determine for each natural language statement whether the statement satisfies a predetermined criterion with respect to stenosis, e.g. whether the statement is classified as positive with respect to stenosis, and responsive to a determination that one or more statements satisfy the predetermined criterion, add images 324, 326, 328 each representing a stenosis to a coronary pictogram template 320 accordingly, thereby to generate a first image 318. The process block 316 outputs the first image 318.

As mentioned above, the first image 318 comprises an image template 320 that has had added thereto images 324, 326, 328 representing the first medical finding. In this example, the image template is a pictogram 320 representing a patient anatomy to which the radiology report is directed. Specifically, in this example, the image template is a 18-segment SCCT (Society of Cardiovascular Computer Tomography) coronary pictogram 320. The pictogram 320 illustrates 17 segments relating to arteries of a human heart, which segments are labelled by number on the pictogram 320. The pictogram includes a key 332 which indicates the name of each segment to which the numbered label corresponds. For example, the key 332 indicates that the label "1" on the pictogram 320 corresponds to the "proximal RCA (right coronary artery)" segment of the pictogram 320.

The images, 324, 326 and 328 added to the pictogram 320 represent the presence of stenosis (i.e. a narrowing in a blood vessel or other structure) on the pictogram 320, and the resulting image 318 thereby indicates the first medical finding of stenosis.

In some examples, the method (e.g. the method performed by process block 316 and/or that described with reference to FIGS. 1 and 2) may comprise analysing the medical text report 314, using the computer-implemented analysis process, to determine, for each natural language statement determined as satisfying the predetermined criterion with respect to a first medical finding, one or more first parameters associated with the first medical finding. For example, the one or more first parameters may include a location parameter, an extent parameter, and or a type parameter, indicating the location, extent and type of the first medical finding (e.g. stenosis) respectively. The adding the image 324, 328, 326 representing the first medical finding to the image template 320 may then be based at least in part on the determined one or more first parameters.

The analysing the medical text report to determine one or more first parameters, such as a location parameter, may be, for example, performed by the computer-implemented analysis process described above to classify a statement of the medical text report 314 as positive or negative with respect to the first medical finding. For example, different classification and/or quantification tasks may be conducted concurrently. For example, a machine learning based classification and/or quantification algorithm may be trained, for example based on the training data 250 as described above, not only to detect the absence or presence of the first medical finding (e.g. a stenosis) in the medical text report 314, but also determine the type, extent and/or location of the stenosis from the natural language text provided in the medical text report 314.

In some examples, at least one of the first parameters may comprise a location parameter relating to a location of the first medical finding. The method may comprise determining, based on the location parameter, a section or segment of the image template 320 to which the image 324, 326, 328 representing the first medical finding is to be added, and adding the image 324, 326, 328 representing the first medical finding to the determined section or segment of the image template 320. For example, the radiology report 314 may include the natural language statement "There is moderate stenosis of the proximal LAD". The process block 316 may analyse this natural language statement and classify the statement as positive with respect to stenosis, and hence that the statement satisfies the predetermined criterion with respect to stenosis. The process block 316 may analyse the statement to determine that a location parameter associated with the first medical finding of stenosis for the natural language statement as "proximal LAD". This may be achieved, for example, in the same way as described above, for example by applying an inferred function (either provided by a trained machine learning algorithm or otherwise) to word-embeddings for words or phrases of the natural language statement. The process block 316 may then add, for example overlay, an image 326 representing the stenosis to the pictogram template 320 at the appropriate section or segment of the pictogram 320. For example, the process block 316 may overlay a two-dimensional shape 326 to the segment labelled 6 (corresponding to the proximal LAD) of the 18-segment SCCT coronary pictogram 320, thereby to generate an image 318 that indicates visually and immediately on the pictogram 320 that there is a stenosis 326 of the proximal LAD. For example, the two-dimensional shape 326 may be dimensioned and positioned on the pictogram template 320 such that the Proximal LAD artery (labelled 6) appears in the image 320 to be narrowed, hence indicating the stenosis. Other images 324, 328 representing other findings may be added at other locations of the pictogram 320 as appropriate.

In some examples, the first parameters may alternatively or additionally comprise one or both of a type parameter relating to a type of the first medical finding and an extent parameter relating to an extent of the first medical finding, and the adding the image 324, 326, 328 representing the first medical finding to the image template 320 may be based at least in part on one or both of the type parameter and the extent parameter. For example, the method may comprise generating the image 324, 326, 328 representing the first medical finding based on one or both of the type parameter and the extent parameter. Continuing with the above example, the radiology report 314 may include the natural language statement "There is moderate stenosis of the proximal LAD". The process block 316 may analyse the statement to determine that an extent parameter associated with the first medical finding of stenosis for the natural language statement as "moderate". This may be achieved, for example, in the same way as described above, for example by applying an inferred function (either provided by a trained machine learning algorithm or otherwise) to word-embeddings for words or phrases of the natural language statement. The process block 316 may then add, for example overlay, an image 326 representing the stenosis to the pictogram template 320 based on the determined extent parameter. For example, the process block 316 may overlay a moderately dimensioned shape 326 to the segment labelled 6 (corresponding to the proximal LAD) of the 18-segment SCCT coronary pictogram 320, thereby to generate an image 318 that indicates visually and immediately on the pictogram 320 that there is a moderate stenosis 326 of the proximal LAD. For example, the two-dimensional shape 326 may be dimensioned and positioned on the pictogram template 320 such that the Proximal LAD artery (labelled 6) appears in the image 320 to be moderately narrowed, hence indicating the moderate stenosis. Alternatively or additionally, the process block may generate the shape 326 or other representation 326 to have a specific colour, for example orange, to visually indicate a moderate stenosis 326 of the proximal LAD. Other images 324, 328 representing other findings may have other sizes, colours and/or other properties as appropriate.

The image 318 may be generated by a computer-implemented image generation process. The image generation process may be in addition to the computer-implemented analysis process described above. The image generation process may use an image generation algorithm. In some examples, the text analysis algorithm may transmit or otherwise output structured data to the image generation algorithm. For example, the text analysis may output information indicating that the text analysis algorithm determined that the text report 314 included one or more natural language statements satisfying the predetermined criterion with respect to the first medical finding (e.g. that stenosis was found), as well as information indicating one or more of the first parameters associated with each of those statements, for example, the location, extent and/or type parameters for each finding.

The image generation algorithm may be configured to accept the structured output information, and generate the image 318 based at least in part thereon. For example, the image generation algorithm may determine from the structured output that the relevant template is an 18-segment SCCT coronary pictogram 320, and therefore retrieve this template from a storage. The image generation algorithm may then use the information indicating one or more of the first parameters, for example, the location, extent and/or type parameters for each finding to overlay appropriate images 324, 326, 328 representing the first medical findings on the appropriate section of the image template 320, thereby to generate the image 318. The process utilising structured output information may allow for the image 318 indicating the first medical finding(s) of the text report 314 to be efficiently produced, and may facilitate distribution of the text analysis and image generation processes.

Figure 4:
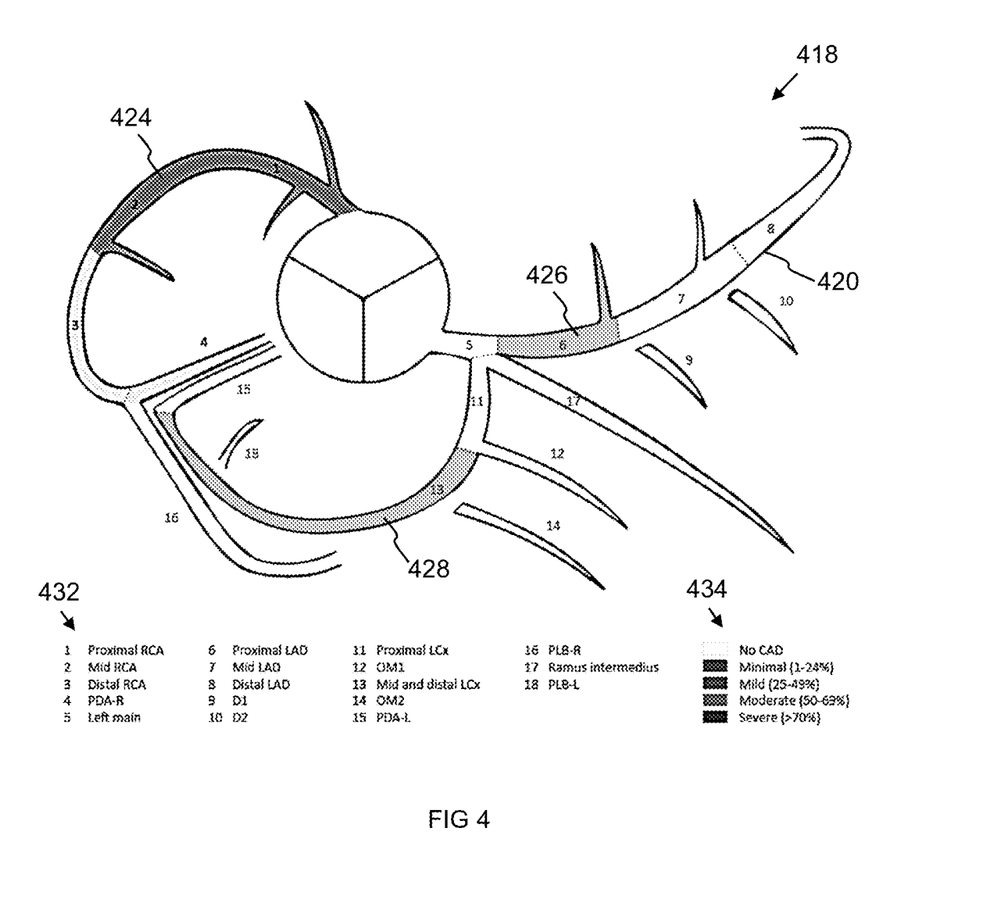
FIG. 4 illustrates schematically a generated image according to an example.

FIG. 4 illustrates schematically a first image 418 that may be generated according to another example. The image 418 may, for example, be generated by the method described above with reference to FIGS. 1 to 3. In this example, as for the first image 318 of FIG. 3, the image template 420 is an 18-segment SCCT coronary pictogram 420, to which has been added images 424, 426, 428 representing the first medical findings of a radiology report (not shown in FIG. 4). In this example, the first medical finding is coronary artery disease (CAD). Again, the image 418 comprises a key 432 that indicates the name of each segment or section of the SCCT coronary pictogram 420 to which the numbered label corresponds.

However, in the example image 418 of FIG. 4, the images 424, 426, 428 representing the first medical findings comprise a filling or colouring or highlighting of the whole segment or section of the coronary pictogram 420 at which the first medical findings are determined to be located (for example based on location parameters determined as described above). For example, in FIG. 4, the whole territory or segment or section of the coronary pictogram 420, labelled 1 and corresponding to the proximal RCA, is coloured, indicating that coronary artery disease (CAD) is present in the proximal RCA (as determined from analysis of the text report (not shown)). The method may therefore add images (e.g. coloured portions) 424, 426, 238 to the image template 420 on a per segment or section basis. This may be useful where it is not possible to determine the precise location of medical finding (for example stenosis) based on the radiology report. The image 418 produced nevertheless indicates clearly, visually, efficiently and immediately the medical findings of the text report in image form.

Further, the example image 418 of FIG. 4 comprises a severity key 434. The severity key comprises a series of coloured boxes with corresponding severity labels. Although no colour is shown in the Figures, a severity label of "No CAD" may be associated with a white box, a severity label of "Minimal (1-24%)" may be associated with a green box, a severity label of "Mild (25-49%)" may be associated with blue box, a severity label of "Moderate (50-69%)" may be associated with an orange box, and a severity label of "Severe (>70%)" may be associated with a red box. The segments or sections labelled 1 and 2, corresponding to the segments "Proximal RCA" and "Mid RCA" of the coronary pictogram 420 are each coloured or filled in orange, indicating that moderate coronary artery disease (CAD) is present in those regions of the heart, and the segments or sections 6 and 13, corresponding to the segments "Proximal LAD" and "Mid and distal LCx" are each coloured or filled in blue, indicating that mild CAD is present in those regions of the heart. The remaining segments of the pictogram 420 are white, indicating no CAD in the remaining regions of the heart. The images 424, 426, 428 representing the first medical findings may be generated by the image generation algorithm to have a specific colour or other severity indicating characteristic based on the severity parameter determined as described above. For example, different images 424, 426, 428 having different colours or other severity indicating characteristics may be stored in advance, and the image generation algorithm may select the appropriate image 424, 426, 428 to add to the image template accordingly. The addition of an image 424, 426, 428 to the template may be based on, for example, the location parameter and the severity parameter output by the text analysis algorithm as described above.

Figure 5:
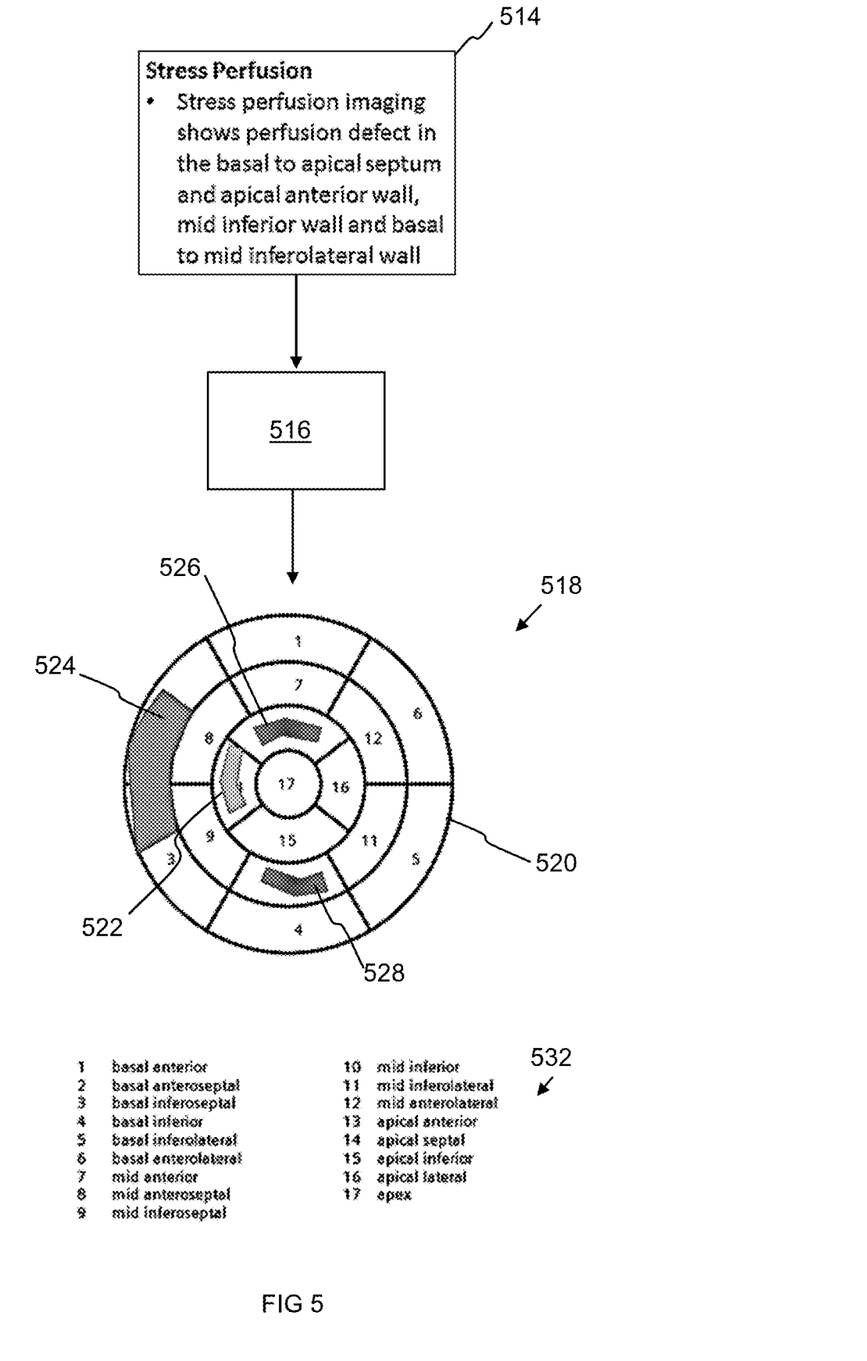
FIG. 5 illustrates schematically a process for generating an image from a medical text report, according to second example.

FIG. 5 illustrates schematically a process including a generated first image 518 according to another example. Similarly to as in the example described above with reference to FIG. 3, in the process of FIG. 5, a medical text report 514 is input into a process block 516, which may carry out the method according to any of the examples described above, thereby to produce a first image 518 comprising an image template 520 to which has been added images 524, 526, 522, 528 representing the first medical finding of the medical text report 514.

However, in the example of FIG. 5, the medical text report 514 is a stress perfusion cardiac MRI report, the first medical finding is "perfusion defect", and the image template is polar plot diagram template 520. The polar plot diagram template 520 comprises polar plot divided into sections (labelled 1 to 17 in FIG. 5). The image 518 comprises a key 532 comprising the labels 1 to 17 each with a description of which heart wall portions the label corresponds. For example, label 1 corresponds to the basal anterior wall. The medical text report 514 comprises the natural language statement "Stress perfusion imaging shows perfusion defect in the basal to apical septum and apical anterior wall, mid inferior wall and basal to mid inferolateral wall". The process block 516 analyses the medical text report 514, for example using a computer-implemented analysis process as described above. The process block 516 determines that the statement satisfies a predetermined criterion with respect to a first medical finding, in this example that the statement is classified as positive with respect to the first medical finding (in this example "perfusion defect"). The process block 516 also determines, e.g. using the computer-implemented analysis process, location parameters for the first medical findings. Responsive to a determination that the statement satisfies the predetermined criterion, the process block 516 adds images 522, 524, 526, 528 representing the first medical finding to the polar plot diagram template 520, thereby to generate the first image 518. The process block 518 determines, based on the location parameters, the sections (labelled 1 to 17 in FIG. 5) of the polar plot diagram template 520 to which the images 522, 524, 526, 528 representing the first medical findings are to be added, and adds the images 522, 524, 526, 528 to the determined sections of the of the polar plot diagram template 520 accordingly. In some examples, the processing block 516 may analyse regionally-varying measurements in the report 514, and add the images 522, 524, 526, 528 accordingly. In this example, the images 522, 524, 526, 528 representing the medical findings are shapes overlaid onto the appropriate section of the polar plot template 520. For example, the one image is a shape 524 that extends over both sections labelled 1 and 2 in FIG. 5, indicating in the generated image 518 that there is a perfusion defect in the basal anteroseptal and inferoseptal walls. Other images 522, 526, 528 are added to the plot template 520 at other locations as appropriate. The image 518 produced indicates clearly, visually, efficiently and immediately the medical findings of the text report in image form.

It will be appreciated that other image templates having other forms than those described above may be used, and that other images, for example images of symbols or the like, representing the first medical finding may be added to the image template, thereby to generate an image indicating the medical findings of the text report in image form. It will also be appreciated that other medical text reports than those described above may be used, for example other pathology reports or other medical imaging reports or the like. As another example (not illustrated), the image template may be or comprise a medical image, for example a CT or other medical scan image, on which the radiology report or other medical text report is based. Image analytics algorithms may be used to detect relevant locations or sections or segments in the medical image. An image representing the medical finding may then be added to, for example overlaid onto, the medical scan image at the appropriate location so as to indicate the medical finding on the medical scan image. For example, an image of an arrow may be added onto the medical scan image so as to indicate the location of the medical finding as identified in the medical text report. As another example, an image of numbers representing measurements relating to the medical finding may be overlaid onto the medical scan image, for example, a diameter of a diseased vessel may annotate a line connecting the vessel walls. In some examples, the method may comprise identifying a portion or section or segment of the medical scan image in which a medical finding is located, and zooming in on or cropping the medical scan image so that the generated image shows the relevant portion or segment or section.

Figure 6:
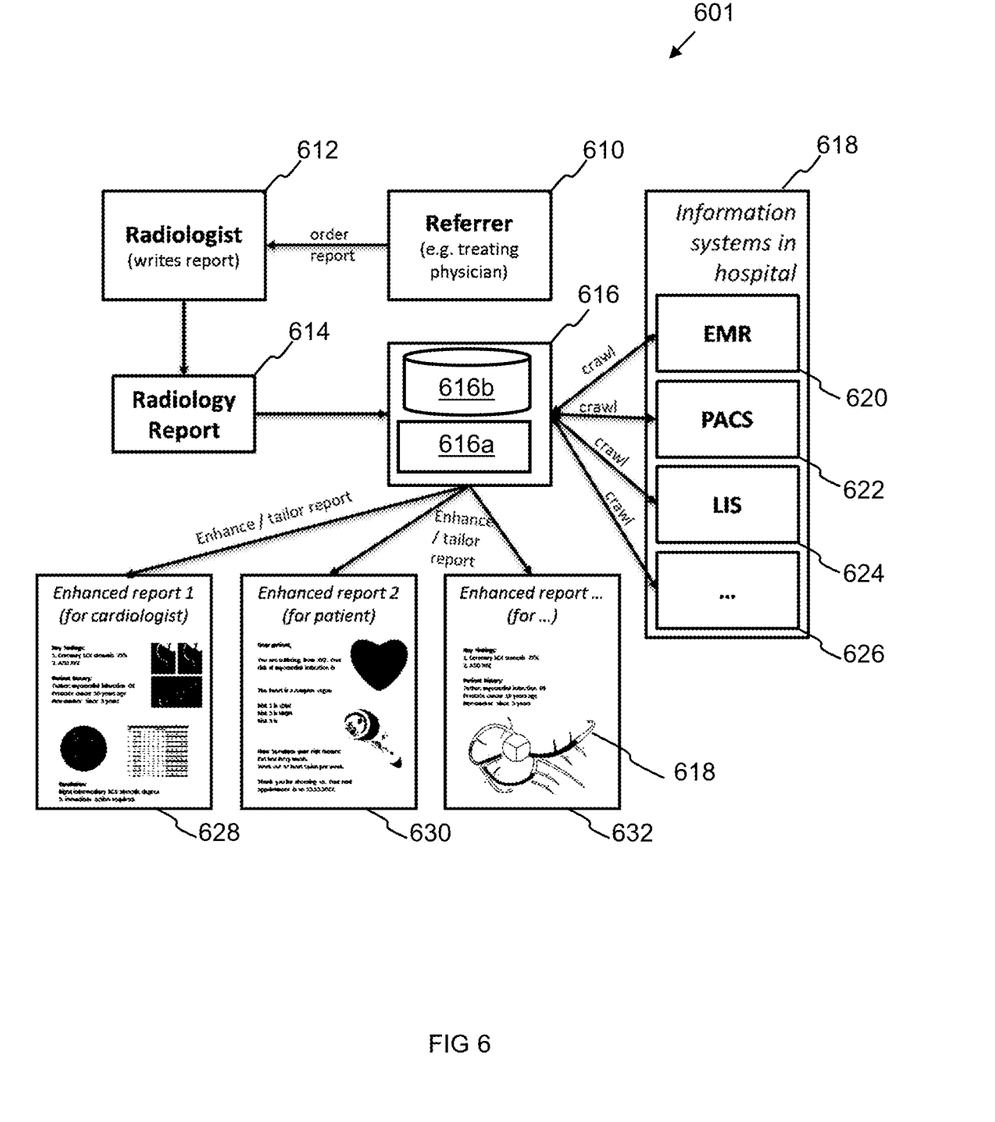
FIG. 6 illustrates schematically a system comprising an apparatus for generating an image from a medical text report, according to an example.

FIG. 6 illustrates schematically a system 601 comprising an apparatus 616 for generating a first image from a medical text report 614, according to an example. The apparatus 616 may be configured to perform the method and/or implement the processing according to any one of the examples described herein. The apparatus 616 may be, for example, a computer. The apparatus 616 comprises a processor 616a and a memory 616b. The memory 616b may store a program which when executed by the processor 616a causes the apparatus 616 to perform the method and/or implement the processing according to any one of the examples described herein.

The system 601 of FIG. 6 comprises a referrer device 610, a radiologist device 612, a radiology report 614, hospital information systems 618, a first enhanced report 628, a second enhanced report 630 and a third enhanced report 632. The hospital information systems 618 comprise an EMR (Electronic Medical Records) system 620, a PACS (Picture Archiving and Communication) system 622, a LIS (laboratory Information) system 624, and other systems 626.

In overview, the referrer device 610, which may be an electronic device operated by a physician treating a patient, may send an order for a report to the radiologist device 612, which may be an electronic device operated by a radiologist. For example, the referrer device 610 may order a CTA radiology report. The radiologist device 612 may receive this order and the radiologist may analyse or read CTA images or other data taken of the patient and produce (for example write or dictate or otherwise) the radiology report 614 comprising one or more natural language statements. The apparatus 616 acquires the radiology report 614, and generates a first image 618 by adding an image representing medical findings determined from the report 614 to an image template, for example using the method described above with reference to FIGS. 1 to 5. In this example, the apparatus 616 generates a plurality of medical reports 628, 630, 632 at least one of which comprises the generated first image 618.

In some examples, a medical report 628, 630, 632 may be generated based on a recipient category. The recipient category may be the category of the intended recipient of the generated medical report 628, 630, 632, such as a "medical expert" category or "patient" category. The medical report 628, 630, 632 may therefore be generated so as to include text and/or generated first images 618 tailored to a recipient of a given category. For example, for a "medical expert" category, the apparatus 616 may be configured to extract from the radiology report 614 a short summary of the most relevant findings structured in a specific, standardized way, using medical language and/or abbreviations to further simplify the report, and include this in the generated medical report 628. The apparatus 616 may apply different report "styles" for different levels of expertise (e.g. junior versus senior cardiologist) or medical specialty. The apparatus 616 may extract key images from the available radiology scans on which the radiology report is based and add these to the report 628. For a "patient" category however, the apparatus 616 may add into the generated report 630 narrative text that explains the findings, contexts and medical terms in an easy-to-understand way, alongside simple graphical illustrations 618 that help understanding the overall context, disease state, and severity of certain findings, even for laypeople. This may allow reports 628, 630, 632 to be specifically tailored to a given recipients' needs or understanding level, thereby allowing for improved information efficiency and/or improved comprehension of the report.

In some examples, different algorithms may be run by the apparatus 616 for different recipient categories. In other examples, an algorithm may be run by the apparatus 616 that has a different configuration for each different recipient category.

In some examples, the information available to the radiologist device 612 and/or the radiologist operating the device 612 may be limited at the time of generating the radiology report 614. For example, only scan images and the reason for referral may be available to the radiologist device 612 and/or radiologist. The radiologist device 612 and/or radiologist may have no access to the referring hospital's IT systems. Hence it may not be possible for a radiologist to include context of the patient's medical details into the radiology report 614, which may be important for the clinical decision-making process by the referrer. Therefore, in some examples, the apparatus 616 may obtain, from a hospital database, for example the hospital information systems 618, medical data of a patient to which the medical text report 614 relates, and add at least a portion of the obtained medical data to one or more of the medical reports 628, 630, 632. This allows for the generated medical reports 628, 630, 632 to include the context of the patient's condition to convey the state and history of the patient, thereby for example improving the efficiency of the clinical decision-making process by the referrer, and for example reducing the risk of misdiagnosis.

In some examples, the apparatus 616 may be connected to the hospital information systems 618, for example each of the EMR system 620, the PACS 622, the LIS 624 and other systems 626. The apparatus 616 may access and crawl one or more of these systems for relevant additional information to add to the enhanced reports 628, 632, 630. For example, the apparatus 616 may crawl available information in IT systems for data relevant to the patient to which the radiology report is directed, for example patient history and the like. The apparatus 616 having access to and crawling the hospital information systems 618 allows the apparatus 616 to add additional relevant information (e.g. patient history, previous findings relevant for correct diagnosis of the current disease, other imaging information, laboratory test results or other tests, etc.) to the generated reports 628, 630, 632 in addition to the generated first image 618, which may improve understanding of the radiology report, and hence may prevent misdiagnosis.

In some examples, the apparatus 616 may include into the reports 628, 630, 632 additional information from other tests found by crawling the hospital information systems 618, for example test reports (e.g. including tables with measurements, or image files). In some examples, the apparatus 616 may process the test reports in a similar manner as the radiology report 614 (e.g. so as to be tailored towards certain audiences). The computer implemented analysis process described above may be applied recursively in order to generate a given report 628, 630, 632. Such additional information may improve decision making (for example in the case of a report tailored to treating physician 628) and also allow the improved narrative for patient-tailored reports 630.

ALTERNATIVE EXAMPLE

According to an alternative example, a method of generating an image from a medical text report comprises: acquiring a medical text report comprising one or more natural language statements; and generating, using a computer implemented image generation process, and based on the one or more natural language statements, the image.

The medical text report may be a radiology report, for example as described above with reference to FIGS. 1 to 6.

The generated image may be used in the same way as for the first image as described above with reference to FIGS. 1 to 6.

In this alternative example, the image may be generated by a Generative Adversarial Network (GAN). The GAN may generate (e.g. synthesize) the image based on visual descriptions, which visual descriptions may comprise the one or more natural language statements of the medical text report. The GAN may be, for example, a deep convolutional GAN (DC-GAN).

The GAN may comprise a generator G that generates (e.g. synthesizes) a synthetic image conditioned on query text (e.g. conditioned on the one or more natural language statements of the medical text report, and/or one or more segments of the natural language statements).

The GAN may comprise a discriminator D that processes the synthetic images provided by the generator G. The discriminator D may attempt to discriminate between the synthetic images provided and training data.

The discriminator D may reject synthetic images or samples of synthetic images that do not fulfil one or more criteria. For example, the one or more criteria may comprise image plausibility criteria, or conditioning criteria. This process may be applied recurrently, thereby to generate the image.

The GAN may be trained for generating the image (for example a key graphic) from medical text reports, for example radiology reports. For example, the GAN may be trained using training data. The training data may comprise a plurality of medical text reports, for example radiology reports, for example stored in a training database.

In some examples, one or more of the medical text reports of the training data comprise one or more natural language statements and an associated key image. The one or more natural language statements may be descriptive of the associated key image. The training of the GAN may be based on the natural language statements using the associated key image as a ground-truth. For example, the one or more natural language statements and/or the associated key image may be extracted from the medical text reports (e.g. radiology reports) and stored in association with one another in a training database.

In some examples, the medical text reports or the training data, or natural language statements from the medical text reports of the training data, may be annotated with ground-truth labels. For example, the ground-truth annotation may be the same or similar to that described above with reference to FIGS. 1 to 6. In one example, the ground-truth labelling of the natural language statements may be a manual process. The training of the GAN may be based on the natural language statements using the annotations as a ground truth.

Generating (e.g. synthesizing) an image directly, for example using a GAN, based on the one or more natural language statements may allow for illustrative images to be generated (e.g. synthesized) directly from medical text reports (e.g. radiology reports), for example without prior knowledge of the precise subject of the radiology report. As for the first image described above with reference to FIGS. 1 to 6, the generated image may enhance understanding of radiology reports and/or may help reduce misdiagnosis based thereon.

An apparatus, for example a computer or processing system, for example comprising a processor and a memory, may be arranged to perform the method according to this alternative example. A program may be provided which, when executed on a computer, causes the computer to perform the method of this alternative example. A computer readable medium may store the program.

The above examples (including those of the alternative example) are to be understood as illustrative examples. It is to be understood that any feature described in relation to any one example may be used alone, or in combination with other features described, and may also be used in combination with one or more features of any other of the examples, or any combination of any other of the examples. Furthermore, equivalents and modifications not described above may also be employed without departing from the scope of the invention, which is defined in the accompanying claims.

The invention claimed is:

1. A method of generating a first image from a medical text report, the method comprising:
    acquiring a medical text report comprising one or more natural language statements;
    determining, using a machine-learned network, for each natural language statement, whether the statement satisfies a predetermined criterion with respect to a first medical finding, the determining by the machine-learned network being whether the first medical finding exists in the natural language statement, the machine-learned network comprising a network architecture previously trained with a machine learning-based algorithm inferring a function from labelled training data of training examples of statements and ground truth labels for each of the statements, the network architecture as previously trained used in the determining;
    responsive to a determination that said statement satisfies the predetermined criterion, adding a visual representation of the first medical finding to an image template representing anatomical structure, the visual representation being an image representation showing the first medical finding as a spatial distribution graphically representing the first medical finding on the image template; and
    communicating the first image having the image added to the image template.

2. The method according to claim 1, wherein the machine-learned network comprises a text classification, and wherein the first predetermined criterion comprises that the statement is classified by the text classification as positive with respect to the first medical finding.

3. The method according to claim 1, wherein the method further comprises:
    determining, using the machine-learned network, for each natural language statement determined as satisfying the predetermined criterion with respect to a first medical finding, one or more first parameters associated with the first medical finding; and
    wherein the adding the image representation of the first medical finding to the image template is based at least in part on the determined one or more first parameters.

4. The method according to claim 3, wherein at least one of the first parameters comprises a location parameter relating to a location of the first medical finding; and the method further comprises:
    determining, based on the location parameter, a section of the image template to which the image representing the first medical finding is to be added; and
    adding the image representation of the first medical finding to the determined section of the image template.

5. The method according to claim 4, wherein the first parameters comprise one or both of a type parameter relating to a type of the first medical finding and an extent parameter relating to an extent of the first medical finding; and the adding the image representation of the first medical finding to the image template is based at least in part on the type parameter, the extent parameter, or both the type parameter and the extent parameter.

6. The method according to claim 5, wherein the adding the image representation of the first medical finding to the image template comprises overlaying the image template with the image representing the first medical finding.

7. The method according to claim 6, wherein acquiring comprises acquiring the medical text report as a radiology report.

8. The method according to claim 7, wherein the image template comprises a pictogram representing a patient anatomy to which the medical text report is directed; and wherein the image representation of the first medical finding is added to the pictogram so as to indicate the first medical finding on the pictogram.

9. The method according to claim 3, wherein the first parameters comprise one or both of a type parameter relating to a type of the first medical finding and an extent parameter relating to an extent of the first medical finding; and the adding the image representation of the first medical finding to the image template is based at least in part on the type parameter, the extent parameter, or both the type parameter and the extent parameter.

10. The method according to claim 1, wherein the adding the image representation of the first medical finding to the image template comprises overlaying the image template with the image representation of the first medical finding.

11. The method according to claim 1, wherein acquiring comprises acquiring the medical text report as a radiology report.

12. The method according to claim 1, wherein the image template comprises a pictogram representing a patient anatomy to which the medical text report is directed; and wherein the image representation of the first medical finding is added to the pictogram so as to indicate the first medical finding on the pictogram.

13. The method according to claim 1, wherein the machine-learned network comprises a recurrent neural network or a generative adversarial network.

14. The method according to claim 13, wherein the method further comprises training the machine-learned network based on a database of textual statements, each statement being annotated with a ground-truth label corresponding to the first medical finding.

15. The method according to claim 14, wherein the training comprises:
    generating, based on a plurality of medical text reports, one or more word-embeddings for one or more words of the plurality of medical text reports; and
    determining, for each of the textual statements, one or more said word embeddings representative of the textual statement; and
    wherein the training is based on the word-embeddings representative of each textual statement.

16. The method according to claim 14, wherein the training is implemented using a Long-Short-Term-Memory based Recurrent Neural Network architecture.

17. The method according to claim 1, wherein the method further comprises:
    generating a medical report, the medical report comprising the first image.

18. An apparatus for generating a first image from a medical text report, the apparatus comprising:
    a memory storing a program;

a processor configured by the program stored in the memory, the program configuring the processor to:

acquire a medical text report comprising one or more natural language statements;

determine, using a machine-trained computer implemented analysis process, for each natural language statement, whether the statement satisfies a predetermined criterion with respect to a first medical finding, the determination by the machine-learned network being whether the first medical finding exists in the natural language statement, the machine-learned network comprising a network architecture previously trained with a machine learning-based algorithm inference of a function from labelled training data of training examples of statements and ground truth labels for each of the statements, the network architecture as previously trained used to determine;

responsive to a determination that said statement satisfies the predetermined criterion, add a visual representation of the first medical finding to an image template representing anatomical structure, the visual representation being an image representation showing the first medical finding as a spatial distribution graphically representing the first medical finding on the image template; and communicate the first image having the image added to the image template.

19. A non-transitory computer readable memory storing a program comprising instructions which when executed on a computer cause the computer to communicate a first image, the memory storing the instructions comprising:

acquiring a medical text report comprising one or more natural language statements;

determining, using a machine-learned network, for each natural language statement, whether the statement satisfies a predetermined criterion with respect to a first medical finding, the determining by the machine-learned network being whether the first medical finding exists in the natural language statement, the machine-learned network comprising a network architecture previously trained with a machine learning-based algorithm inferring a function from labelled training data of training examples of statements and ground truth labels for each of the statements, the network architecture as previously trained used in the determining;

responsive to a determination that said statement satisfies the predetermined criterion, adding a visual representation of the first medical finding to an image template representing anatomical structure, the visual representation being an image representation showing the first medical finding as a spatial distribution graphically representing the first medical finding on the image template; and communicating the first image having the image added to the image template.

* * * * *